United States Patent [19]

Faré et al.

[11] 4,157,092
[45] Jun. 5, 1979

[54] DIRECT-ACTING RESPIRATOR

[75] Inventors: Angelo Faré; Giovanni Fumagalli, both of Milan, Italy

[73] Assignee: Hoffmann-La Roche Inc., Nutley, N.J.

[21] Appl. No.: 729,574

[22] Filed: Oct. 4, 1976

[30] Foreign Application Priority Data

Oct. 24, 1975 [CH] Switzerland ............... 13793/75

[51] Int. Cl.² .......................................... A61M 16/00
[52] U.S. Cl. .............................. 128/145.6; 417/454; 417/472; 92/128
[58] Field of Search ............... 128/145.6, 145.7, 145.8, 128/145.5, 142, 142.3, 202, 188, 273, 30, 30.2, 2.08; 417/454, 472; 92/128

[56] References Cited

U.S. PATENT DOCUMENTS

| 3,039,399 | 6/1962 | Everett | 128/DIG. 3 |
|---|---|---|---|
| 3,057,346 | 10/1962 | Goodner | 128/145.6 |
| 3,467,078 | 9/1969 | Bird et al. | 128/145.6 X |
| 3,651,804 | 3/1972 | Spiller | 128/145.6 |
| 3,658,443 | 4/1972 | Fumagalli | 417/384 |
| 3,818,806 | 6/1975 | Fumagalli | 128/145.6 X |
| 3,985,133 | 10/1976 | Jenkins et al. | 128/214 F |
| 3,993,061 | 11/1976 | O'Leary | 128/214 F |

FOREIGN PATENT DOCUMENTS

| 636448 | 12/1963 | Belgium. | |
|---|---|---|---|
| 663814 | 5/1963 | Canada. | |
| 174883 | 1905 | Fed. Rep. of Germany | 417/472 |
| 270393 | 1913 | Fed. Rep. of Germany | 417/472 |
| 1012841 | 7/1952 | France. | |
| 515723 | 1/1972 | Switzerland. | |
| 616914 | 1/1949 | United Kingdom | 417/454 |
| 924556 | 4/1963 | United Kingdom | 417/472 |
| 1016718 | 1/1966 | United Kingdom. | |
| 1157331 | 7/1969 | United Kingdom. | |
| 1324163 | 7/1973 | United Kingdom. | |
| 1443152 | 7/1976 | United Kingdom. | |

OTHER PUBLICATIONS

Drager, "Spiromat" prospectus, p. 566, Jan. 1961.
Drager, "Spiromat" prospectus, p. 5661, Aug. 1965.

Primary Examiner—Henry J. Recla
Attorney, Agent, or Firm—Jon S. Saxe; Bernard S. Leon; Mark L. Hopkins

[57] ABSTRACT

Direct-acting respirator arrangement capable of convenient sterilization in minimal time following each use, through structuring which permits integral removal of those component parts of the respirator that come into contact with the respiratory gas flow. There is provided a fixed structure incorporating a pump unit which is comprised of a variable volume chamber having a fixed wall part supported in the structure and a movable wall part operatively connected to a driven reciprocating movement element. The fixed wall part of the chamber is rigidly attached to a member through which at least the chamber feed and delivery lines extend. The member is provided with means enabling releasable connection to the structure. The movable wall part is provided with means for releasable connection to the reciprocating element.

5 Claims, 5 Drawing Figures

DIRECT-ACTING RESPIRATOR

BACKGROUND OF THE INVENTION

Various kinds of apparatus are known whereby patients, the injured, and others whose physiological respiratory activity is insufficient or inadequate, are treated with assisted and/or controlled respiration. These devices, which are generally known as artificial respirators, include, among their essential components or apparatus, a pump system which includes a chamber having an alternately variable volume, and a drive means which produces the required cyclic change in the internal volume of the chamber, generally by means of a mechanism which converts the rotary movement of a motor into a reciprocating rectilinear or arcuate movement.

The direct-acting respirators are one category of such devices, in which the gas mixture blow cyclically into the patient's bronochopulmonary system flows through the variable-volume chamber and the appropriate inlet and outlet valves, the respirator thus actng directly as a pumping means to supply the patient with the gases required for the respiratory function, such gases being complemented if required by therapeutic, anaesthetic or other effects.

The devices coming under this category require careful sterilization between successive periods of utilization of all those parts with which the mixture blown into the patient's respiratory system comes into contact (the internal walls of the variable-volume chamber, which is generally formed by a bellows, valves and pipelines). Since it is clearly impossible to subject the entire apparatus to the treatments of complete sterilization in an autoclave (although such treatments would be highly desirable since they have considerable effect even on encapsulated spores) and because the difficulties are obvious in connection with removing the components, the electric motor etc., sterilization is usually carried out via forced circulation by pumping highly toxic and bactericidal gases, such as formalin vapors, nitrogen, compounds, etc. through the variable-volume chamber, the valves and the pipelines.

These sterilization operations based on a flow of gas must be followed by careful flushing out with neutralizing gaseous active substances, such as ammonia vapors, then air, the strictest asepsis conditions being observed at all times.

These requirements in respect of care of respirators mean that tedious and difficult operations have to be performed, while gases are required which are dangerous to store and handle, and in addition there are long periods of interruption in the operation and availability of the respirator.

SUMMARY OF THE INVENTION

The principal object of this invention is to propose a respirator construction which allows convenient sterilization after each use of the device, the times during which the device is unusable between successive periods of use being reduced to a minimum.

According to the invention, there is provided a direct-acting device for assisted and controlled respiration, having a fixed structure incorporating a pump unit which consists of a variable-volume chamber having a fixed wall part supported in said structure and a movable wall part connected to an element receiving a reciprocating movement from a drive means, which is characterized in that said fixed wall part of said chamber is rigidly attached to a unit through which at least the chamber feed and delivery lines extend, said unit being provided with means for releasable connection to said structure and said movable wall part being provided with means for releasable connection to said reciprocating element.

BRIEF DESCRIPTION OF THE DRAWINGS

For a better understanding of the objects and features of the invention, exemplified embodiments are shown in the accompanying drawings and will be described hereinafter. In the drawings.

DESCRIPTION OF THE PREFERRED EMBODIMENT(S)

Figure 1:
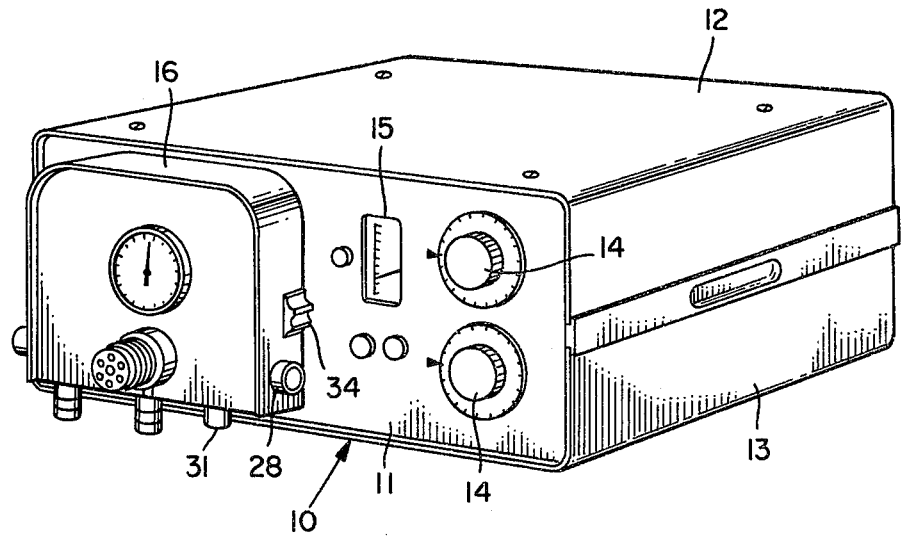
FIGS. 1 and 2 are perspective views of a respirator according to the invention in two different positions.

As shown in FIG. 1, the device having the general reference 10 comprises a casing formed by an end wall 11 and a top and bottom half 12, 13 respectively.

Controls 14 and signal elements 15 are provided on the end wall to monitor and show the working conditions of the device.

Figure 3:
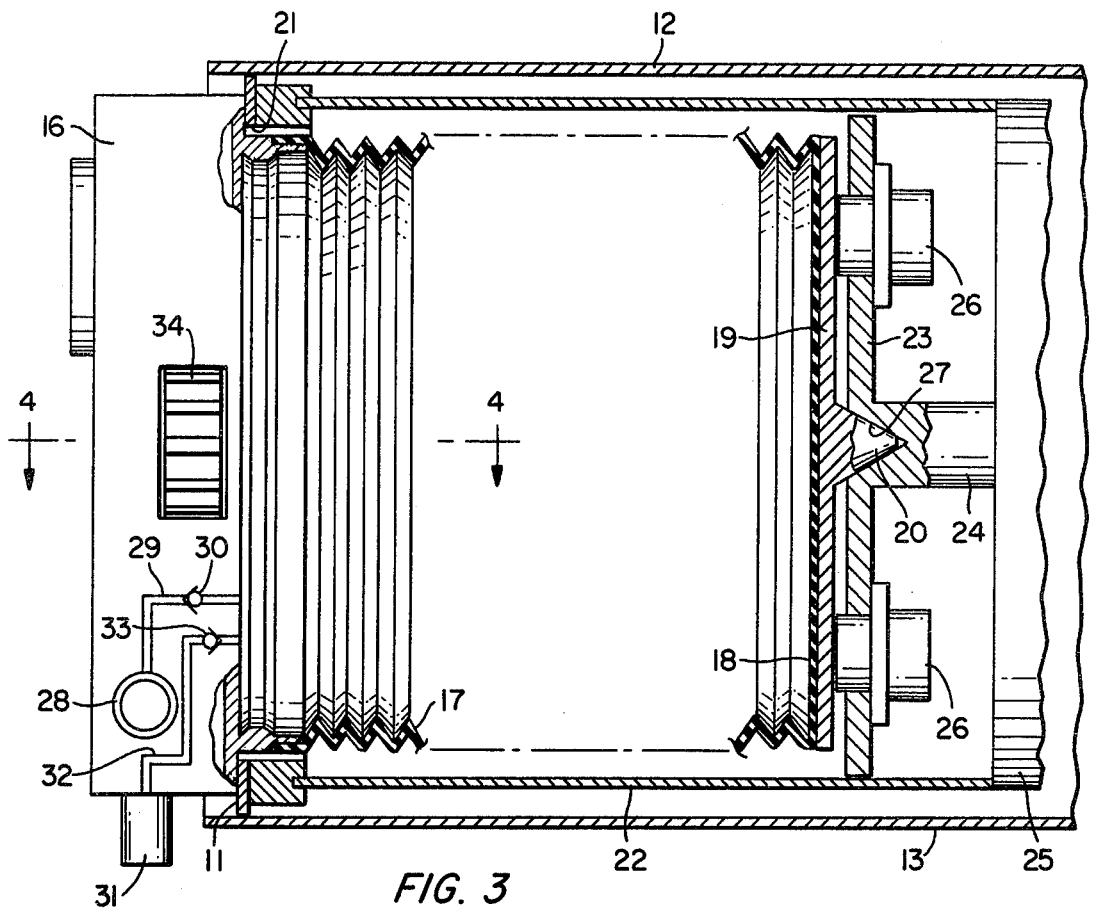
FIG. 3 is a side elevation in partial section of the device shown in FIG. 1.
Figure 4:
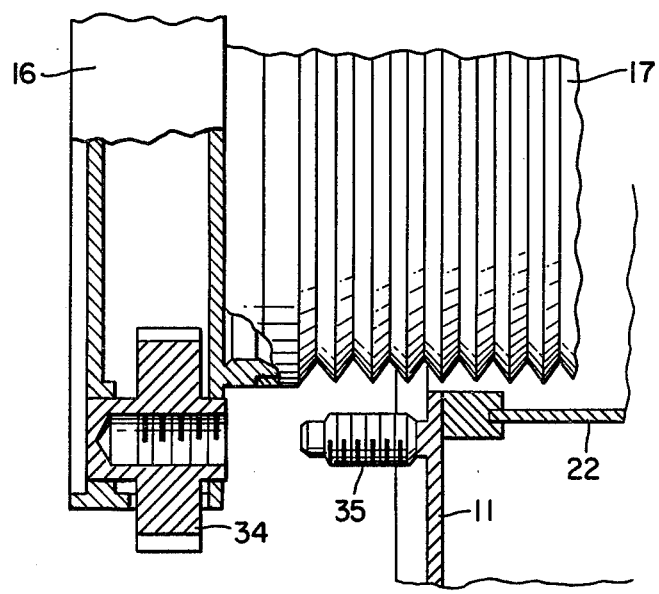
FIG. 4 is a section on the line 4—4 in FIG. 3, some of the parts being shown in exploded form.

A unit 16 shown in detail in FIGS. 3 and 4 is also fixed to the end wall.

A bellows 17 of elastic material, e.g. rubber, is secured to the unit 16 and is sealed off by an end 18 secured to a disc 19 of ferromagnetic material. Disc 19 has a conical projection 20.

End wall 11 has an aperture 21 of a larger diameter than the diameter of the bellows 17. A cylindrical wall 22 is secured around the aperture 21 and a disc 23 moves therein, being borne by a rod 24 to which an axially reciprocating movement is transmitted by drive means 25. Permanent magnets 26 are also secured to the disc 23 and project from the side of the disc remote from the side connected to the rod 24. Disc 23 also has a central recess 27 matching the projection 20 of the disc 19.

The variable volume chamber formed by the bellows 17 is connected to the exterior via lines provided in the unit 16 and monitored by appropriate valves. For example, the drawing diagrammatically shows a connection 28 of a feed line 29 monitored by a valve 30 and a connection 31 on the pressure side, the line of which is monitored by valve 33.

Unit 16 is anchored to the wall 11 of the device by means of rings 34 which are rotatable therein and which have a screwthreaded bore to receive screw bolts 35 projecting from the wall itself.

The operation of the device described will be apparent from the construction of the blown s bronchopulmonary thus acting The device in the operative position is shown in FIGS. 1 and 3. The end 18 of the bellows automatically follows the reciprocating movement of the disc 23, the magnets 26 of which retain the disc 19.

Figure 2:
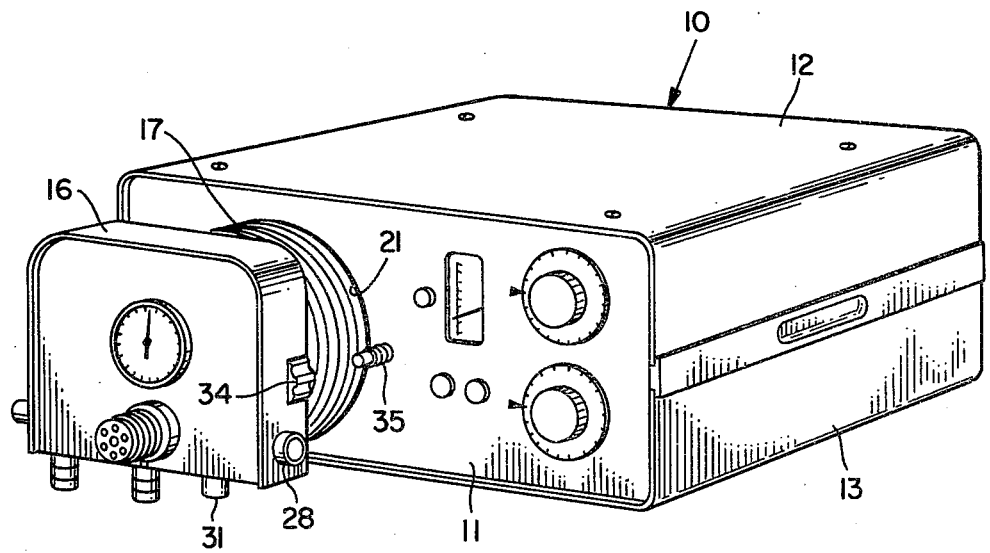

If the screw rings 34 are unscrewed, the unit 16 can be removed from the wall 11 (FIGS. 2 and 4) and the bellows can be removed through the aperture 21, the disc 19 being separated from the magnets simply by pulling it.

The unit 16 can thus be placed together with the bellows 17 in an autoclave or be subjected to some other disinfecting treatment.

In the meantime the respirator can be equipped with a different pump unit 16–17 without the device itself necessarily being rendered unusable for the relatively long disinfection time, according to the objects of the invention.

To enable a unit 16 together with its corresponding bellows to be coupled to the device at any time, the bellows is simply introduced into the aperture 21 and the unit 16 secured to the wall 11, the screw rings 34 being screwed on to the screw bolts 35. The bellows 17 is generally borne by the wall 22 and during its reciprocating movement the disc 23 comes into contact with the disc 19 which is centered by the connection of the projection 20 with the recess 27, and is engaged by the magnets 26 without any difficult manual operations.

Figure 5:
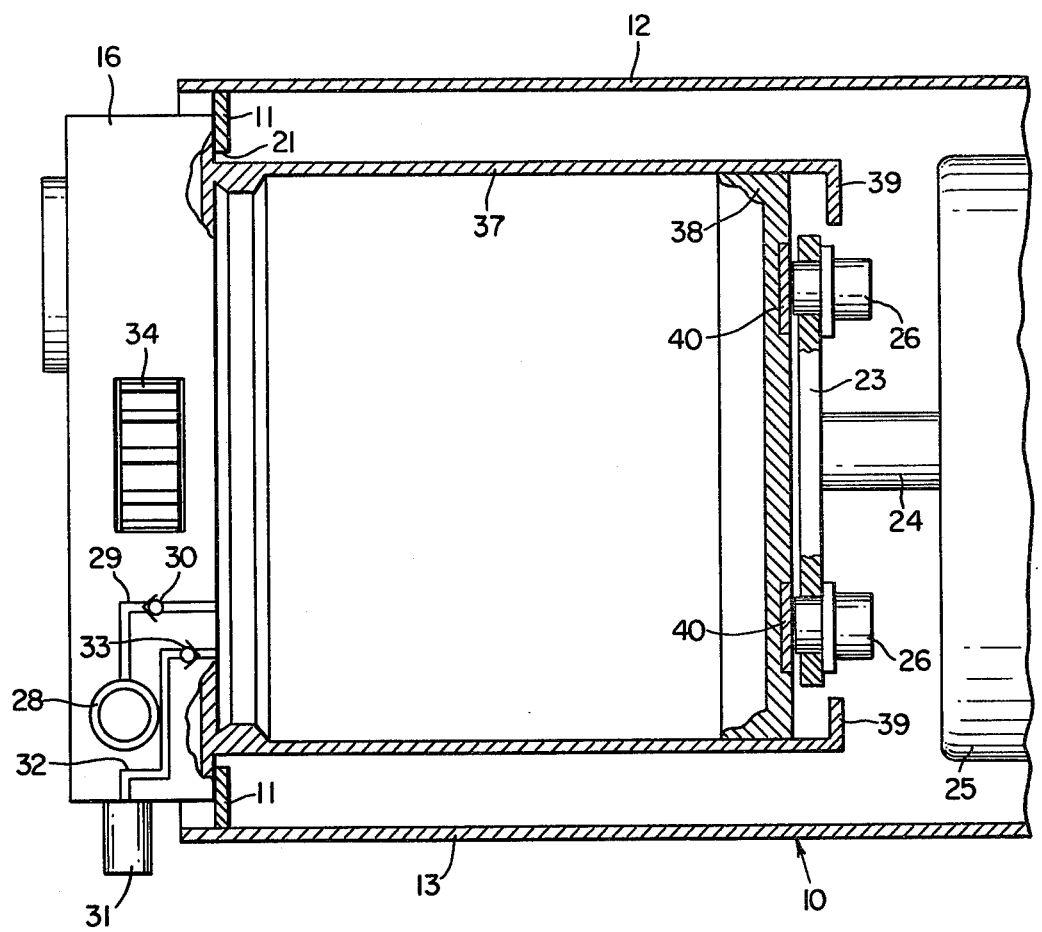
FIG. 5 is a partially sectioned side elevation of another embodiment of the respirator device according to the invention.

The principles according to the invention can also be applied to different constructions of pump chambers. FIG. 3 showing another construction of the invention. FIG. 5 shows components of the device which are equivalent to those of the devices shown in FIGS. 1 to 4.

In this case, a cylinder 37 is secured to the unit 16 and a piston 38 is slidable therein, its removal being prevented by an edge strip 39. At the back, near the pole shoes of the magnets 26 of the disc 23, the piston 38 is provided with an annular insert 40 of ferromagnetic material.

The rigidity of the cylinder 37 means that if required there is no need for any guide wall 22 or centering element of the kind shown by the connection 20–27 in FIG. 3. However, centering elements may be provided between the piston 38 and the disc 23 if they should prove necessary.

The insert 40 is unnecessary if the piston or its entire rear is made of ferromagnetic material.

The device for assisted respiration according to the invention has been explained quite diagrammatically with reference to the components according to the invention, but the device would, of course, be provided with the usual means and accessories which are known in the art.

More particularly, in addition to the said feed and pressure conduits, the unit 16 may include all additional inlets, e.g. for the intake of special gas mixtures, monitoring instruments, valves monitored for the patient's inhalation, and all those components of the respiratory gas circuit which are usually provided in devices of this kind and are intended for sterilization.

Because of the special construction provided according to the invention, only the component parts of the respiratory circuit, i.e. the distribution unit within the unit made of a material suitable for the proposed sterilization, which can be carried out in a gas atmosphere and at temperatures and pressures which the respirator could not withstand as a whole.

The connecting means for the walls 18, 38 of the pump chamber 17, 13 and the drive disc 23 for the reciprocating movement, have been as coupling elements with a magnetic effect by way of example, and this magnetic effect may be permanent-magnetic or electromagnetic. However, the coupling means may have the most diverse constructions and be purely mechanical couplings providing a rigid pressure connection which is, however, releasable without difficult manual operations. Various forms of coupling based on screws, clamping means, and so on, may be provided instead of the connections using screw rings as shown at 34.

What is claimed is:

1. In a respirator for assisted and controlled respiration, having a fixed structure incorporating a pump unit with means defining a variable-volume chamber which has a fixed wall part supported in said structure and a movable wall part operatively associated with said fixed wall part, drive means for providing a reciprocating movement and coupling means connecting said movable wall part to said drive means whereby, said movable wall part is reciprocably movable with respect to said fixed wall part, wherein the improvement comprises a connector unit having rigidly attached thereto said fixed wall part of said means defining said chamber and having means for providing readily releasable connection to said structure, gas feed and delivery lines extending through said connecting unit and said fixed wall part and communicating with said variable volume chamber, and said coupling means comprising a direct-contacting, quick disconnecting coupling arrangement operatively associated between said movable wall part and said drive means and engageable solely by a linear movement of one of said movable wall part and said drive means relative to the other.

2. Respirator according to claim 1 wherein said coupling means between the movable wall part and said drive means is comprised of pairs of elements having mutual magnetic attraction, each element of each pair being opposingly secured to a respective one of said movable wall portion and said drive means.

3. Respirator according to claim 2 wherein said chamber is defined by a bellows of elastically resilient material, the one end of said bellows consisting of a substantially rigid wall which forms the movable wall part of the chamber.

4. Respirator according to claim 2 wherein said movable wall part and said drive means include centering means which are opposingly and complementarily interfitted when said pairs of elements having mutual magnetic attraction are coupled to each other.

5. Respirator according to claim 1 wherein said connector unit has attached thereto connections extending from said feed and delivery lines for pipelines, which connections communicate with the interior of the chamber, and valve means in said feed and delivery lines for providing opposite flows, respectively, therethrough.

* * * * *